(12) United States Patent
Kunin

(10) Patent No.: US 8,337,821 B2
(45) Date of Patent: Dec. 25, 2012

(54) COMPOSITION FOR TREATMENT OF HYPERHIDROSIS

(75) Inventor: Audrey Kunin, Mission Hills, KS (US)

(73) Assignee: DERMAdoctor, Inc., Kansas City, MO (US)

( * ) Notice: Subject to any disclaimer, the term of this patent is extended or adjusted under 35 U.S.C. 154(b) by 240 days.

(21) Appl. No.: 12/844,705

(22) Filed: Jul. 27, 2010

(65) Prior Publication Data

US 2011/0020415 A1 Jan. 27, 2011

Related U.S. Application Data

(60) Provisional application No. 61/228,791, filed on Jul. 27, 2009.

(51) Int. Cl.
*A61K 8/02* (2006.01)
*A61K 8/18* (2006.01)
*A61K 8/26* (2006.01)
*A61K 8/28* (2006.01)
*A01N 25/34* (2006.01)

(52) U.S. Cl. .............. 424/65; 424/66; 424/68; 424/401; 424/402

(58) Field of Classification Search .................. None
See application file for complete search history.

(56) References Cited

U.S. PATENT DOCUMENTS 6,911,195 B2 * 6/2005 Vu et al. .......................... 424/65

* cited by examiner

*Primary Examiner* — Susan Tran
(74) *Attorney, Agent, or Firm* — Husch Blackwell LLP

(57) ABSTRACT

A composition for treatment of hyperhidrosis is provided that contains an effective amount of an antiperspirant. In particular, one embodiment of the composition of the present invention includes an antiperspirant, at least one muscle relaxing agent, at least one peptide, and at least one botanical agent and the composition is applied to a substrate. In another non-limiting illustration, the composition includes from about 0.001 to 50.0 vol % aluminum zirconium tetrachlorohydrex glycine and more preferably 19.0 vol %, glycerin, dipeptide diaminobutyroyl benzylamide diacetate, gamma amino butyric acid, *solanum lycopersicum* (tomato) extract, *gynostemma pentaphyllum* extract, *panax ginseng* root extract, *portulaca oleracea* extract, butylene glycol, denatured alcohol, and water.

3 Claims, No Drawings

COMPOSITION FOR TREATMENT OF HYPERHIDROSIS

CROSS-REFERENCE TO RELATED APPLICATIONS

This application is a nonprovisional of and claims priority to the U.S. Provisional Patent Ser. No. 61/228,791, filed Jul. 27, 2009, which document is hereby incorporated by reference in its entirety to the extent permitted by law.

BACKGROUND OF THE INVENTION

Hyperhidrosis is a medical condition characterized by abnormally increased perspiration, in excess of that required for regulation of body temperature. Hyperhidrosis can either be generalized or localized to specific parts of the body. The face, underarms, palms, soles, areas under the breasts, cleavage and groin areas are most commonly affected. Sweaty hands due to anxiety from dates, job interviews and other unexpected or stressful situations may be embarrassing. In addition, sweat marks and stains under arms and breasts and around the inner thighs can be embarrassing. Hyperhidrosis can have severe physiological consequences such as cold and clammy hands, dehydration, and skin infections secondary to maceration of the skin. Hyperhidrosis can also have devastating emotional effects on one's individual life. Affected people are constantly aware of their condition and try to modify their lifestyle to accommodate this problem. This can be disabling in professional, academic and social life, causing daily embarrassments.

There are many different over-the-counter and prescription products available to treat hyperhidrosis. Some of these products use aluminum chloride which is typically used in regular antiperspirants. However, effectively treating hyperhidrosis requires solutions with high concentrations of aluminum chloride for which irritation is a common side effect. Most prescription drugs known to reduce hyperhidrosis, such as, for example, oxybutynin and glycopyrrolate, have side effects that can include drowsiness, visual symptoms and dryness in the mouth and other mucus membranes. Another type of treatment is injecting botulinum toxin type A which disables sweat glands by blocking the release of the neurotransmitter from the nerve endings that causes the glands to produce sweat. However, this treatment requires needles and medical monitoring and usually lasts from four to nine months. There is also an elective surgery called endoscopic thoracic sympathectomy (ETS) currently available to treat hyperhidrosis. The most common secondary effect of ETS is compensatory sweating. In addition, sometimes the original problem returns after six months due to nerve regeneration. A process called iontophoresis is a procedure that typically uses water to conduct an electric current to the skin that combats production of sweat. A device is used to apply the current for ten to twenty minutes per session, initially with two to three sessions per week followed by a maintenance program of treatments at one to three week intervals, depending upon the user's response.

Therefore, it would be beneficial to have a topical treatment that contains an effective amount of medication to prevent excessive sweating despite being inactive. It would also be beneficial to have a treatment for hyperhidrosis that alleviates the need for cumbersome or time-consuming anti-sweating devices, ineffective topical prescriptions, costly and painful injections and/or invasive surgery. It would be further beneficial to have a topical treatment for the treatment of hyperhidrosis that has little to no harmful side effects.

Sweating caused by hyperhidrosis or by excessive sweat due to the heat and humidity of the environment can cause make-up to be removed from the skin or "melt" away. Therefore, it would be beneficial to have a topical treatment that aids in maintaining make-up for people that excessively sweat or for anyone with sweats caused by hot and humid days.

SUMMARY OF THE INVENTION

The present invention is generally directed to a composition for treatment of hyperhidrosis. The composition hereof contains an effective amount of an antiperspirant. In particular, one embodiment of the composition of the present invention includes an antiperspirant, at least one muscle relaxing agent, at least one peptide, and at least one botanical agent and the composition is applied to a substrate. In another non-limiting illustration, the composition includes from about 0.001 to 50.0 vol % aluminum zirconium tetrachlorohydrex glycine and preferably about 19.0 vol %, glycerin, dipeptide diaminobutyroyl benzylamide diacetate, gamma amino butyric acid, *solanum lycopersicum* (tomato) extract, *gynostemma pentaphyllum* extract, *panax ginseng* root extract, *portulaca oleracea* extract, butylene glycol, denatured alcohol, and water.

Other and further objects of the invention, together with the features of novelty appurtenant thereto, will appear in the course of the following description.

DETAILED DESCRIPTION OF THE INVENTION

There is provided herein a composition for the treatment of hyperhidrosis that substantially eliminates excessive sweating and wetness. The composition hereof generally includes an antiperspirant, at least one muscle relaxing agent, at least one peptide, and at least one botanical agent wherein the composition is applied to a substrate for application to a user's skin. The substrate may be made of, but is not limited to, paper, non-woven fabric, woven fabrics, cloth, polymer film, sponge, formed plastics or other appropriate material. In one embodiment the composition impregnates the substrate. It will be appreciated by those skilled in the art that some agents disclosed throughout this disclosure may have two or more properties.

The composition of the present invention is designed to minimize excessive sweating with the least possible side effects. In one embodiment, the composition contains an effective amount of an antiperspirant. In certain embodiments, the composition contains from about 0.001 to 50.0 vol % and preferably about 19.0 vol % aluminum zirconium tetrachlorohydrex glycine. At that percentage, aluminum zirconium tetrachlorohydrex glycine is a high-potency antiperspirant.

In one embodiment, the composition includes an effective amount of a muscle relaxing agent. In certain embodiments, the muscle relaxing agent may also have nerve inhibiting properties. In certain embodiment, the muscle relaxing agent is present in an amount of from about 0.001 to 80.0 vol % of the composition, more preferably from about 0.01 to 60.0 vol %, and most preferably from about 0.1 to 50.0 vol %. In certain other embodiments, the muscle relaxing agent is gamma amino butyric acid, *panax ginseng* root extract, *solanum lycopersicum* (tomato) extract, ginsenoside Rg3, beta phenyl gamma amino butyric acid, baclofen, picamilon, phosphatidyl choline, GABAB receptor ligands, agonists, gamma butyrolactone, phenibut, deramciclane, hyperforin, tiagabine, gabaculine, phenelzine, valproate, vigabatrin, lemon balm, pregabalin, gabapentin, L-glutamine, picamilon, progabide, tetanospasmin, derivatives thereof, or mixtures thereof. Gamma amino butyric acid helps improve the body's ability to resist the temptation to sweat. *Panax ginseng* root extract is an Asian root that helps the body to cope with stress.

In one embodiment, the composition includes an effective amount of a peptide. In other embodiments, the peptide is present in an amount of from about 0.001 to 80.0 vol % of the composition, more preferably from about 0.01 to 60.0 vol %, and most preferably from about 0.1 to 50.0 vol %. In certain other embodiments, the peptide is dipeptide diaminobutyroyl benzylamide diacetate, argiriline, syn-ake, snap 8 peptide, snap 7 peptide, snap 25 peptide, agrin binding site blockers in MuSK (muscle specific kinase), hexapeptide-30, arginine, calcium channel blockers, dantrolene sodium, methoxyverapamil, diacetate, acetyl octapeptide-3, derivatives thereof, or mixtures thereof. Dipeptide diaminobutyroyl benzylamide diacetate is a small peptide that mimics the activity and effect of the Temple Viper venom.

In one embodiment, the composition includes an effective amount of a botanical agent. In certain embodiment, the botanical agent is present in an amount of from about 0.001 to 80.0 vol % of the composition, more preferably from about 0.01 to 60.0 vol %, and most preferably from about 0.1 to 50.0 vol %. In certain other embodiments, the botanical agent is *portulaca oleracea* extract, *gynostemma pentaphyllum* extract, derivatives thereof, or mixtures thereof. *Portulaca oleracea* extract is rich in potassium and derived from a West African botanical. *Gynostemma pentaphyllum* extract contains saponins and delivers additional benefits.

In certain embodiments, the composition may also include from about 0.1 to about 99.9 vol % of an additive such as, for example, fragrance, denatured alcohol, water, glycerin, and butylene glycol.

In one embodiment, the composition hereof includes about 19% aluminum zirconium tetrachlorohydrex glycine, dipeptide diaminobutyroyl benzylamide diacetate, gamma amino butyric acid, *solanum lycopersicum* (tomato) extract, *gynostemma pentaphyllum* extract, *panax ginseng* root extract, *portulaca oleracea* extract, butylene glycol, denatured alcohol, and water.

Clinical Study

One embodiment of the present invention was clinically tested to demonstrate that a user, having applied the composition to the skin, developed few, if any, side effects. The standards used for inclusion in the study included individuals who were not currently under a doctor's care; individuals who were free of any dermatological or systemic disorder that would interfere with the results; individuals who were free of any acute or chronic disease that would interfere with or increase the risk of study participation; individuals who completed a preliminary medical history form mandated by BCS and were in generally good health; individuals who read, understood and signed an informed consent document relating to the specific type of study; and individuals who were able to cooperate with the investigator and research staff, were willing to have test materials applied according to the study protocol, and completed the full course of the study. The standards for exclusion from the study were individuals who were under 18 years of age; individuals who were currently under a doctor's care; individuals who were currently taking any medication (topical or systemic) that might mask or interfere with the test results; individuals who had a history of any acute or chronic disease that might interfere with or increase the risk associated with study participation; individuals who were diagnosed with chronic skin allergies; and female volunteers who indicated that they were pregnant or lactating. Fifty-one subjects were enrolled in the study and fifty completed the study. The subjects ranged in age from twenty-one to sixty-three. The population demographics of the study were ten males and forty-one females.

The following procedure was followed by the subjects. Subjects were requested to bathe or wash as usual before arrival at the facility. 0.2 mL or 0.2 g of the test material is dispensed onto the occhisive, hypoallergenic patch. The patches containing the test material were then affixed directly to the skin of the infrascapular regions of the hack, to the right or left of the midline, and subjects were dismissed with instructions not to wet the test area or expose it to direct sunlight. Subjects were instructed to remove the patches approximately 24 hours after application. This procedure was repeated until a series of nine (9) consecutive, 24-hour exposures had been made three (3) times a week for three (3) consecutive weeks. Prior to each reapplication, the test sites were evaluated by trained laboratory personnel. In the event of an adverse reaction, the area of erythema and edema were measured. Edema is estimated by the evaluation of the skin with respect to the contour of the unaffected normal skin. Reactions are scored just before applications two through nine and the next test date following application nine. In most instances this is approximately 24 hours after patch removal. Clients are notified immediately in the case of adverse reaction and determination is made as to treatment program if necessary. Following a 10-14 day rest period, a retest/challenge dose was applied once to a previously unexposed test site. The retest dose is equivalent to any one of the original nine exposures. Reactions are scored 24 and 48 hours after application. Comparison is made between the nine inductive responses and the retest dose.

The following scoring system was used and the scoring scale.

| | |
|---|---|
| 0 | No evidence of any effect |
| ? | (Barely perceptible) minimal faint (light pink) uniform or spotty erythema |
| 1 | (Mild) pink uniform erythema covering most of contact site |
| 2 | (Moderate) pink\red erythema visibly uniform in entire contact area |
| 3 | (Marked) bright red erythema with accompanying edema, petechiae or papules |
| 4 | (Severe) deep red erythema with vesiculation or weeping with or without edema |
| D | Patch eliminated due to reaction |
| Dc | Discontinued due to absence of subject on application date |
| M- | Patch applied to an adjacent site after strong test reaction |
| N/A - | Score is not calculated for subjects discontinued before challenge |
| S | Skin stained from pigment in product |
| T - | Tan |

NOTE: All technical employees of AMA LABORATORIES, INC. are required to take and pass a visual discrimination examination conducted by a Board Certified Ophthalmologist using the Farnsworth-Munsell 100 Hue Test as published; which determines a person's ability to discern color against a black background. This test was additionally modified to include a flesh tone background more nearly approaching actual use conditions, wherein erythematous skin is graded according to intensity.

A summary of the results is shown in Table 1:

TABLE 1

| No. | Subject ID | RA | SE | | | | | | | | | | | | Score |
|---|---|---|---|---|---|---|---|---|---|---|---|---|---|---|---|
| 1 | 00 | 0002 | C | F | 0 | 0 | 0 | 0 | 0 | 0 | 0 | 0 | 0 | 0 | 0 |
| 2 | 28 | 0971 | H | F | 0 | 0 | 0 | 0 | 0 | 0 | 0 | 0 | 0 | 0 | 0.0 |
| 3 | 31 | 9721 | H | F | 0 | 0 | 0 | 0 | 0 | 0 | 0 | 0 | 0 | 0 | 0.0 |

TABLE 1-continued

| No. | Subject ID | RA | SE | | | | | | | | | | | | Score |
|---|---|---|---|---|---|---|---|---|---|---|---|---|---|---|---|
| 4 | 34 | 7405 | C | F | 0 | 0 | 0 | 0 | 0 | 0 | 0 | 0 | 0 | 0 | 0.0 |
| 5 | 36 | 1827 | C | F | 0 | 0 | 0 | 0 | 0 | 0 | 0 | 0 | 0 | 0 | 0.0 |
| 6 | 36 | 9728 | H | F | 0 | 0 | 0 | 0 | 0 | 0 | 0 | 0 | 0 | 0 | 0.0 |
| 7 | 38 | 1226 | C | F | 0 | 0 | 0 | 0 | 0 | 0 | 0 | 0 | 0 | 0 | 0.0 |
| 8 | 38 | 4338 | C | F | 0 | 0 | 0 | 0 | 0 | 0 | 0 | 0 | 0 | 0 | 0.0 |
| 9 | 40 | 0533 | C | F | 0 | 0 | 0 | 0 | 0 | 0 | 0 | 0 | 0 | 0 | 0.0 |
| 10 | 40 | 1274 | C | F | 0 | 0 | 0 | 0 | 0 | 0 | 0 | 0 | 0 | 0 | 0.0 |
| 11 | 40 | 6489 | C | F | 0 | 0 | 0 | 0 | 0 | 0 | 0 | 0 | 0 | 0 | 0.0 |
| 12 | 42 | 8196 | C | M | 0 | 0 | 0 | 0 | 0 | 0 | 0 | 0 | 0 | 0 | 0.0 |
| 13 | 44 | 9258 | C | F | 0 | 0 | 0 | 0 | 0 | 0 | 0 | 0 | 0 | 0 | 0.0 |
| 14 | 46 | 2567 | C | F | 0 | 0 | 0 | 0 | 0 | 0 | 0 | 0 | 0 | 0 | 0.0 |
| 15 | 46 | 8520 | C | F | 0 | 0 | 0 | 0 | 0 | 0 | 0 | 0 | 0 | 0 | 0.0 |
| 16 | 48 | 1605 | C | F | 0 | 0 | 0 | 0 | 0 | 0 | 0 | 0 | 0 | 0 | 0.0 |
| 17 | 48 | 3275 | H | F | 0 | 0 | 0 | 0 | 0 | 0 | 0 | 0 | 0 | 0 | 0.0 |
| 18 | 48 | 3746 | C | F | 0 | 0 | 0 | 0 | 0 | 0 | 0 | 0 | 0 | 0 | 0.0 |
| 19 | 48 | 7214 | C | M | 0 | 0 | 0 | 0 | 0 | 0 | 0 | 0 | 0 | 0 | 0.0 |
| 20 | 50 | 1386 | C | F | 0 | 0 | 0 | 0 | 0 | 0 | 0 | 0 | 0 | 0 | 0.0 |
| 21 | 50 | 5772 | C | M | 0 | 0 | 0 | 0 | 0 | 0 | 0 | 0 | 0 | 0 | 0.0 |
| 22 | 52 | 6562 | C | F | 0 | 0 | 0 | 0 | 0 | 0 | 0 | 0 | 0 | 0 | 0.0 |
| 23 | 54 | 2951 | C | F | 0 | 0 | 0 | 0 | 0 | 0 | 0 | 0 | 0 | 0 | 0.0 |
| 24 | 54 | 4408 | C | F | 0 | 0 | 0 | 0 | 0 | 0 | 0 | 0 | 0 | 0 | 0.0 |
| 25 | 54 | 5333 | C | F | 0 | 0 | 0 | 0 | 0 | 0 | 0 | 0 | 0 | 0 | 0.0 |
| 26 | 56 | 5529 | C | F | 0 | 0 | 0 | 0 | 0 | 0 | 0 | 0 | 0 | 0 | 0.0 |
| 27 | 58 | 8637 | C | F | 0 | 0 | 0 | 0 | 0 | 0 | 0 | 0 | 0 | 0 | 0.0 |
| 28 | 60 | 1825 | C | F | 0 | 0 | 0 | 0 | 0 | 0 | 0 | 0 | 0 | 0 | 0.0 |
| 29 | 60 | 3008 | C | M | 0 | 0 | 0 | 0 | 0 | 0 | 0 | 0 | 0 | 0 | 0.0 |
| 30 | 60 | 3430 | C | F | 0 | 0 | 0 | 0 | 0 | 0 | 0 | 0 | 0 | 0 | 0.0 |
| 31 | 60 | 3986 | C | F | 0 | 0 | 0 | 0 | 0 | 0 | 0 | 0 | 0 | 0 | 0.0 |
| 32 | 60 | 7847 | C | F | 0 | 0 | 0 | 0 | 0 | 0 | 0 | 0 | 0 | 0 | 0.0 |
| 33 | 62 | 1313 | H | F | 0 | 0 | 0 | 0 | 0 | 0 | 0 | 0 | 0 | 0 | 0.0 |
| 34 | 62 | 3596 | C | F | 0 | 0 | 0 | 0 | 0 | 0 | 0 | 0 | 0 | 0 | 0.0 |
| 35 | 62 | 5537 | C | F | 0 | 0 | 0 | 0 | 0 | 0 | 0 | 0 | 0 | 0 | 0.0 |
| 36 | 64 | 0347 | C | M | 0 | 0 | 0 | 0 | 0 | 0 | 0 | 0 | 0 | 0 | 0.0 |
| 37 | 64 | 8003 | H | F | 0 | 0 | 0 | 0 | 0 | 0 | 0 | 0 | 0 | 0 | 0.0 |
| 38 | 66 | 8507 | c | M | 0 | 0 | 0 | 0 | 0 | 0 | 0 | 0 | 0 | 0 | 0.0 |
| 39 | 68 | 4139 | C | F | 0 | 0 | 0 | 0 | 0 | 0 | 0 | 0 | 0 | 0 | 0.0 |
| 40 | 68 | 7705 | C | F | 0 | 0 | 0 | Dc | Dc | Dc | Do | Dc | Dc | Dc | Dc |
| 41 | 68 | 8917 | C | F | 0 | 0 | 0 | 0 | 0 | 0 | 0 | 0 | 0 | 0 | 0.0 |
| 42 | 70 | 2436 | H | M | 0 | 0 | 0 | 0 | 0 | 0 | 0 | 0 | 0 | 0 | 0.0 |
| 43 | 70 | 3392 | C | F | 0 | 0 | 0 | 0 | 0 | 0 | 0 | 0 | 0 | 0 | 0.0 |
| 44 | 72 | 2865 | C | M | 0 | 0 | 0 | 0 | 0 | 0 | 0 | 0 | 0 | 0 | 0.0 |
| 45 | 72 | 3637 | H | F | 0 | 0 | 0 | 0 | 0 | 0 | 0 | 0 | 0 | 0 | 0.0 |
| 46 | 72 | 7479 | C | M | 0 | 0 | 0 | 0 | 0 | 0 | 0 | 0 | 0 | 0 | 0.0 |
| 47 | 74 | 1746 | C | M | 0 | 0 | 0 | 0 | 0 | 0 | 0 | 0 | 0 | 0 | 0.0 |
| 48 | 76 | 7818 | H | F | 0 | 0 | 0 | 0 | 0 | 0 | 0 | 0 | 0 | 0 | 0.0 |
| 49 | 7$ | 5826 | C | F | 0 | 0 | 0 | 0 | 0 | U | 0 | 0 | 0 | 0 | 0.0 |
| 50 | 80 | 0282 | A | F | 0 | 0 | 0 | 0 | 0 | 0 | 0 | 0 | 0 | 0 | 0.0 |
| 51 | 80 | 4176 | C | F | 0 | 0 | 0 | 0 | 0 | 0 | 0 | 0 | 0 | 0 | 0.0 |

The clinical study provided the observation that there were no adverse reactions of any kind reported during the course of the study. The study concluded that, under the conditions of the study, there were no identifiable signs or symptoms of sensitization (contact allergy) noted for the sweat treatment.

From the foregoing, it will be seen that this invention is one well adapted to attain all ends and objects hereinabove set forth together with the other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative, and not in a limiting sense.

What is claimed is:

1. A composition for treatment of hyperhidrosis consisting essentially of:
   about 19.0 vol % aluminum zirconium tetrachlorohydrex glycine;
   gamma amino butyric acid;
   *panax ginseng* root extract;
   dipeptide diaminobutyroyl benzylamide diacetate;
   *portulaca oleracea* extract;
   *solanum lycopersicum* (tomato) extract; and
   *gynostemma pentaphyllum* extract;
   wherein said composition impregnates a substrate.

2. The composition of claim 1 wherein said substrate is selected from a group consisting of paper, non-woven fabric, and woven fabric.

3. The composition of claim 1 wherein said composition further consisting essentially of denatured alcohol, water, glycerin, and butylene glycol, as additive agents.

* * * * *